United States Patent
Kopperschmidt et al.

(10) Patent No.: US 9,731,061 B2
(45) Date of Patent: Aug. 15, 2017

(54) METHOD AND DEVICE FOR MONITORING EXTRACORPOREAL BLOOD FLOW

(71) Applicant: FRESENIUS MEDICAL CARE DEUTSCHLAND GMBH, Bad Homburg (DE)

(72) Inventors: Pascal Kopperschmidt, Dittelbrunn (DE); Thomas Núrnberger, Burkardroth (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 102 days.

(21) Appl. No.: 14/893,292

(22) PCT Filed: May 16, 2014

(86) PCT No.: PCT/EP2014/060171
§ 371 (c)(1),
(2) Date: Nov. 23, 2015

(87) PCT Pub. No.: WO2014/187755
PCT Pub. Date: Nov. 27, 2014

(65) Prior Publication Data
US 2016/0095971 A1    Apr. 7, 2016

(30) Foreign Application Priority Data

May 23, 2013   (DE) .......... 10 2013 008 720

(51) Int. Cl.
*A61M 37/00* (2006.01)
*A61M 1/36* (2006.01)

(52) U.S. Cl.
CPC ........ *A61M 1/3656* (2014.02); *A61M 1/3639* (2013.01); *A61M 2205/17* (2013.01);
(Continued)

(58) Field of Classification Search
CPC .............. A61M 1/3656; A61M 1/3639; A61M 1/3653; A61M 1/14; A61M 2205/17;
(Continued)

(56) References Cited

U.S. PATENT DOCUMENTS

| 6,077,443 A | 6/2000 | Goldau |
| 6,445,304 B1 | 9/2002 | Bandeian, Jr. |

(Continued)

FOREIGN PATENT DOCUMENTS

| DE | 102006032815 A1 | 1/2008 |
| EP | 0 995 451 A2 | 4/2000 |

(Continued)

OTHER PUBLICATIONS

International Search Report from PCT/EP2014/060171, mailed Jul. 4, 2014.

*Primary Examiner* — Philip R Wiest
(74) *Attorney, Agent, or Firm* — Kilyk & Bowersox, P.L.L.C.

(57) ABSTRACT

A method and a device for monitoring an extracorporeal blood flow during an extracorporeal blood treatment with an extracorporeal blood treatment device. The extracorporeal blood treatment device may include the device for monitoring an extracorporeal blood flow. The arterial and/or venous patient access is monitored with a first and a second method, each of which there is a check for a presence of at least one criterion that is characteristic of a condition of the vascular access that is not in proper order, the criteria for the first and second methods being distinguished from one another. A blood pump, which is preferably an occlusion blood pump, is stopped once the presence of the at least one criterion of the first method has been established, while a venous cut-off unit remains open. Once the blood pump has been stopped, the presence of the at least one criterion is checked with the second method. The venous cut-off unit is not closed until (Continued)

the at least one criterion for the second method is present. Otherwise the blood pump is restarted to continue the blood treatment.

21 Claims, 1 Drawing Sheet

(52) U.S. Cl.
CPC ..... *A61M 2205/18* (2013.01); *A61M 2230/04* (2013.01); *A61M 2230/06* (2013.01)

(58) Field of Classification Search
CPC ...... A61M 2205/18; A61M 2205/3306; A61M 2205/3317; A61M 2205/3375; A61M 2205/3569; A61M 2205/359; A61M 2230/04; A61M 2230/062
USPC ................................................ 604/4.01–6.16
See application file for complete search history.

(56) References Cited

U.S. PATENT DOCUMENTS

| | | | | |
|---|---|---|---|---|
| 6,649,063 | B2* | 11/2003 | Brugger | A61M 1/3462 |
| | | | | 210/645 |
| 7,276,041 | B2* | 10/2007 | Moll | A61B 5/02042 |
| | | | | 210/646 |
| 8,603,020 | B2* | 12/2013 | Roger | A61M 1/3653 |
| | | | | 604/4.01 |
| 2012/0271161 | A1 | 10/2012 | Buckberry | |

FOREIGN PATENT DOCUMENTS

| | | |
|---|---|---|
| WO | 9710013 A1 | 3/1997 |
| WO | 2006008866 A1 | 1/2006 |
| WO | 20080006559 A1 | 1/2008 |
| WO | 20090127683 A1 | 10/2009 |
| WO | 20100149726 A2 | 12/2010 |
| WO | 20110116943 A1 | 9/2011 |

* cited by examiner

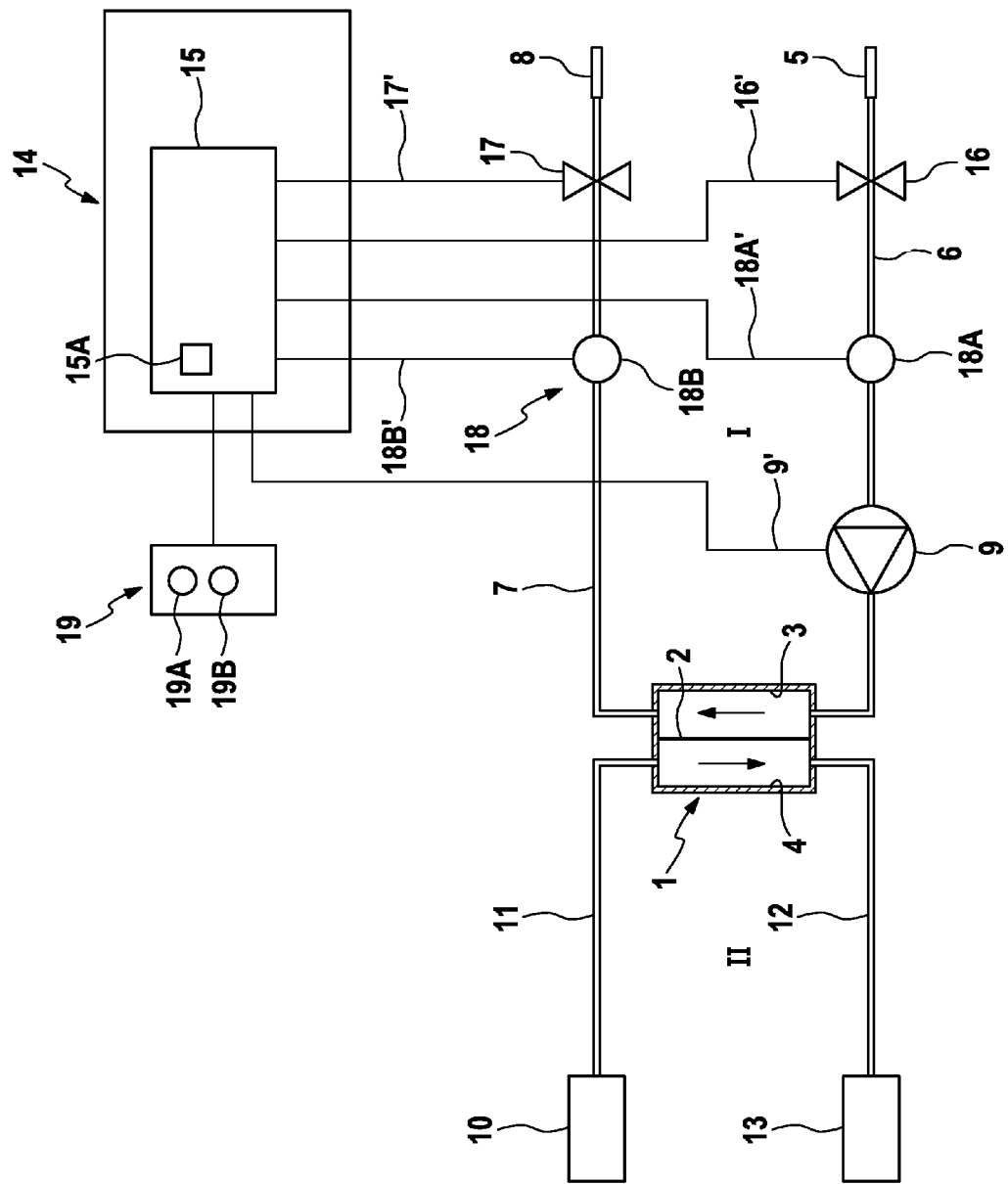

METHOD AND DEVICE FOR MONITORING EXTRACORPOREAL BLOOD FLOW

CROSS REFERENCE TO RELATED APPLICATIONS

The present application is the national stage entry of International Patent Application No. PCT/EP2014/060171, filed on May 16, 2014, the disclosure of which is expressly incorporated herein in its entirety by reference thereto, and claims priority to Application No. DE 10 2013 008 720.1, filed in the Federal Republic of Germany on May 23, 2013.

FIELD OF INVENTION

The present invention relates to a method for monitoring extracorporeal blood flow during an extracorporeal blood treatment with an extracorporeal blood treatment device. The present invention furthermore relates to a device for monitoring extracorporeal blood flow for an extracorporeal blood treatment device and to an extracorporeal blood treatment device with a device for monitoring extracorporeal blood flow.

BACKGROUND

Various devices are known in the field of medicine with which it is possible to remove fluids from the patient or supply fluids to the patient via a tube. Access to the patient is generally gained with a catheter inserted into bodily organs or with a cannula for puncturing blood vessels. Proper access to the patient must be ensured during the procedure or treatment. Therefore it is necessary to monitor the patient access.

Extracorporeal blood treatment devices in particular that involve an extracorporeal blood flow require proper access to the patient. Among known extracorporeal blood treatment devices are for instance dialysis systems and cell separators that require an access to the vascular system of the patient. During extracorporeal blood treatment, blood is removed from the patient for instance using an arterial tube with an arterial puncture cannula, and the blood is re-supplied to the patient via a venous tube with a venous puncture cannula. The arterial and venous accesses to the patient may also be monitored during use of a double lumen catheter, which is employed especially for acute extracorporeal blood treatment.

Monitoring devices that function based on very different principles are known for monitoring the patient access. However, it is common to all of these monitoring devices that they check whether a specific criterion is present that is considered characteristic of the vascular access not being in proper order.

Known from International Patent Publication No. WO 2006/008866 A1 and U.S. Pat. No. 6,445,304 B1 are monitoring devices that assume as a characteristic criterion for a patient access that is in proper order that the skin of the patient is not moist at the puncture site. Therefore these monitoring devices have a moisture sensor that is placed on the skin of the patient at the puncture site. Certainly the moisture sensor will detect blood escaping at the puncture point if a patient access is not in proper order. However, it is disadvantageous that unintentional wetting of the puncture location with a fluid may lead to a false alarm.

To monitor a patient access, other monitoring devices evaluate characteristic variables that are measured in the arterial and/or venous branch of the extracorporeal blood flow. Monitoring devices are known that monitor the pressure in the arterial and/or venous branch as the characteristic variable. When there is an increase in pressure or a drop in pressure it is assumed that the vascular access is not in proper order. Moreover, monitoring devices are known that monitor characteristic pressure pulses in the arterial and/or venous branch of the extracorporeal blood flow. These pressure pulses are produced in the extracorporeal blood flow or may derive from physiological events in the patient who is connected to the extracorporeal blood flow. For instance, it is known to monitor pressure pulses in the extracorporeal blood flow, which pulses are produced in the extracorporeal flow by the running blood pump or are produced outside of the blood flow by the heartbeat of the patient.

Monitoring devices that monitor the change in pressure or pressure pulses in the extracorporeal blood flow are described in International Patent Publication No. WO 97/10013, International Patent Publication No. WO 2009/127683 A1 and International Patent Publication No. WO 2010/149726 A2, for instance.

EP 0 995 451 B1 suggests for increasing certainty simply combining a method based on monitoring the arterial and venous pressures with other methods for detecting a faulty vascular access. International Patent Publication No. WO 2009/127683 A1 suggests detecting a plurality of characteristic variables and, for monitoring, using pressure pulses that derive from the patient's heartbeat and pressure pulses produced by the running blood pump.

SUMMARY

The underlying object of the present invention is to increase the safety of the extracorporeal blood treatment and to reduce the risk of a false alarm, as well.

The present inventive method and the present inventive device assume that the arterial and/or venous access is being monitored with a first and with a second method, in which methods the presence of at least one criterion that is characteristic of a vascular access condition that is not in proper order is checked, the criteria of the first method and of the criteria of the second method being distinguished from one another. A patient access that is not in proper order is established based on monitoring with the first and second methods, vascular access that is not in proper order being established when both the at least one criterion for the first method and the at least one criterion for the second method are present. The reliability of detecting a vascular access that is not in proper order is improved due to the increased redundancy.

The present inventive method and the present inventive device provide that the blood treatment cannot be interrupted by closing the venous cut-off unit in the venous branch of the extracorporeal blood flow unless a vascular access that is not in proper order can be detected with a high degree of certainty. Otherwise the blood treatment is not interrupted by closure of the venous cut-off unit. In practice this is advantageous when the venous cut-off unit of the known blood treatment devices, due to a fault, changes to a defined closure condition that should only permit the closure to be opened by manual intervention performed by medical staff according to required measures.

With the present inventive method and the present inventive device, first only the blood pump, which is preferably an occlusion blood pump, is stopped once the presence of the at least one criterion of the first method has been established, while the venous cut-off unit remains open, however. The presence of the at least one criterion for the second method is checked once the blood pump has been stopped. The venous cut-off unit is not closed unless the at least one criterion for the second method is present. Otherwise the blood pump is restarted to continue the blood treatment. Since the cut-off unit does not need to be opened once the blood pump has been started, the blood treatment may be continued without manual intervention. In contrast, if the puncture cannula has slipped out of the vascular access, i.e., there really is a fault, no more blood can be advanced out of the venous tube by means of the pump once the preferably occlusion blood pump has stopped, even if the cut-off unit is not yet closed. This increases the safety of the blood treatment overall and avoids unnecessary interruptions in the blood treatment.

In the present invention, the arterial branch of the extracorporeal blood flow with the arterial patient connection shall be understood to be the line and needle with which blood is removed from the patient, and the venous branch of the extracorporeal blood flow with the venous patient connection shall be understood to be the return line and needle with which blood is returned to the patient. This definition of the terms "arterial branch of the extracorporeal blood flow with the arterial patient connection" and "venous branch of the extracorporeal blood flow with the venous patient connection" therefore refer equally to arterio-venous and veno-venous accesses.

In blood treatment devices that, in addition to the venous cut-off unit, also have an arterial cut-off unit, once the at least one criterion for the first method has been established, the arterial and venous cut-off units remain open, the arterial and venous cut-off units being closed when the at least one criterion of the second method is present.

One preferred embodiment provides an acoustic, visual or tactile alarm if there is a disruption, the alarm being generated once the presence of the at least one criterion of the second method has been established.

In one particularly preferred embodiment, a first electrical alarm signal is generated once the presence of the at least one criterion for the first method has been established, and a second electrical alarm signal is generated once the presence of the at least one criterion for the second method has been established. The first alarm signal may trigger a preliminary alarm, for instance a visual alarm, especially an indicator on the control panel of the dialysis machine or a recording, for indicating a potential complication to the medical staff. The medical staff is thus alerted early to a possible disruption and can take the required measures after the second alarm, at the latest.

For the present invention it is irrelevant which criteria form the basis for the first method and for the second method for monitoring the blood flow. The first method and the second method may be any desired methods for monitoring vascular access. In principle, the establishment of a faulty vascular access does not have to be verified with just one additional method; it may also be verified with a plurality of methods. Naturally the presence of one criterion for a vascular access that is not in proper order is equivalent to the absence of a criterion for a vascular access that is in proper order.

The at least one criterion for the first and/or second method may be a change in a characteristic variable that is measured in the arterial and/or venous branch of the extracorporeal flow or outside of the arterial and/or venous branch of the extracorporeal flow at the venous and/or arterial puncture site. In this context, a change in a variable is also includes the variable no longer being present after the fault.

The characteristic variable may be the change in pressure or the change in pressure pulses in the arterial and/or venous branch of the extracorporeal flow as a function of the condition of the arterial and/or venous access. For instance, a drop in blood pressure may be detected during a continuous blood pressure measurement. The pressure pulses produced by the running blood pump or by the heartbeat of the patient may be measured. Pressure pulses for monitoring the blood flow may also be produced by brief opening and/or closing of the cut-off units or an intentional change in the type of conveyance by the blood pump or in the ultrafiltration rate. Moreover, it is possible to produce brief temperature fluctuations in the blood flow.

The present inventive method and the present inventive device have proved particularly advantageous when the second method for verifying the presence of a vascular access that is not in proper order is based on monitoring the change in pressure pulses measured in the arterial and/or venous branch of the extracorporeal flow that derive from a physiological event in the patient connected to the extracorporeal flow, especially the heartbeat of the patient. Stopping the blood pump when the cut-off units are opened creates the optimum requirements for measuring the pressure pulses that derive from a physiological event in the patient. Since these pressure pulses are not measured when the blood pump is running, the pressure pulses, which have relatively small amplitudes compared to the pressure pulses produced by the blood pump, are not overlaid by pulses from the blood pump. Consequently it is not necessary to separate these pressure pulses from the pulses from the blood pump using a relatively complex signal analysis.

In one particularly preferred embodiment, the pressure pulses produced by the heartbeat of the patient are measured in the arterial and venous branch of the extracorporeal flow, the amplitude of the pressure pulses measured in the arterial branch being compared to a first limit and the amplitude of the pressure pulses measured in the venous branch being compared to a second limit, the blood pump only being restarted if both the amplitude of the pressure pulses measured in the arterial branch are greater than the first limit and the amplitude of the pressure pulses measured in the venous branch are greater than the second limit. Monitoring both the arterial branch and the venous branch of the blood flow ensures that the blood treatment is not continued unless the presence of a fault can be ruled out with a high degree of certainty.

Another particularly preferred embodiment provides for the venous cut-off unit, and where necessary also the arterial cut-off unit, to be closed once the blood pump has stopped when a prespecified time interval has elapsed. Consequently it must be established within a window of time that there is no fault so that the blood pump can be restarted.

The present inventive device for monitoring the extracorporeal blood flow has a control and computing unit that is configured such that the method steps required for performing the present inventive method are executed. The control and computing unit may be a data processing unit, for instance a microprocessor, on which a data processing program runs.

The variables relevant for the monitoring may be detected with the known measuring units. The monitoring device has a pressure measuring unit for measuring pressure, for instance.

The present inventive monitoring device is preferably a component of the extracorporeal blood treatment device, so that the monitoring device can make use of the components present in the blood treatment device. The control and computing unit in the monitoring device may then be a component of the central control and computing unit for the blood treatment device. The required components are controlled with control signals that shall be understood to be all signals with which commands or measured values may be transmitted.

An exemplary embodiment of the present invention shall be explained in greater detail in the following, referring to the sole FIGURE that depicts the essential components of an extracorporeal blood treatment device that has a device for monitoring the extracorporeal blood flow.

FIG. 1 shows an exemplary embodiment of an extracorporeal blood treatment device, especially a hemodialysis device, that has a device for monitoring the vascular access. In the present exemplary embodiment the monitoring device is a component of the hemodialysis device.

DETAILED DESCRIPTION

The hemodialysis device has as the blood treatment unit a dialyzer or filter 1 that is divided into a blood chamber 3 and a dialysate chamber 4 by a semipermeable membrane 2. An arterial tube 6 is connected by means of an arterial puncture cannula 5 as the patient connection to the patient's fistula or shunt (not shown) and leads to an inlet to the blood chamber 3 of the dialyzer 1. A venous tube 7 that is connected by means of a venous puncture cannula 8 as the patient connection to the patient's fistula or shunt goes out from the outlet of the blood chamber 3 in the dialyzer 1. A blood pump 9 is connected to the arterial tube 6 and pumps the blood in the extracorporeal blood flow I. The blood pump 9 is preferably an occlusion pump. The arterial and venous tubes form the arterial and venous branches 6, 7, respectively, of the extracorporeal blood flow.

The dialysate flow II in the dialyzer includes a dialysate source 10 to which a dialysate supply line 11 is connected that leads to the inlet for the dialysate chamber 4 for the dialyzer. A dialysate outlet line 12 leads from the outlet of the dialysate chamber 4 of the dialyzer 1 to an outlet 13. A dialysate pump (not shown) is connected to the dialysate outlet line 12.

The dialysis device is controlled with a central control and computing unit 14 that has a microprocessor that is programmed such that the steps required for controlling the individual components and for detecting and evaluating measured values are performed. In the present exemplary embodiment, the control and computing unit 15 in the monitoring device is a component of the central control and computing unit 14 for the dialysis device.

An arterial cut-off unit 16 is provided on the arterial tube 6 downstream of the arterial cannula 5 and upstream of the blood pump 9, and a venous cut-off unit 17 is provided on the venous tube 7 upstream of the venous cannula 8. The cut-off units 16, 17, may be electromagnetically actuatable tube clamps. In principle the arterial cut-off unit 16 may omitted, however.

The monitoring device also has a pressure measuring unit 18 that has [ . . . ] via an arterial pressure sensor 18A and a venous pressure sensor 18B, that are configured for measuring the pressure in the arterial and venous tubes 6, 7.

In addition, the monitoring device has an alarm unit 19 that in the present exemplary embodiment is a component of the alarm unit for the blood treatment device. The alarm unit 19 has a first signal generator 19A and a second signal generator 19B. The first signal generator 19A provides only a preliminary alarm, for instance only a visual signal, an indication on the screen of the machine, or a corresponding recording, while the second signal generator 19B provides an acoustic and/or visual and/or tactile alarm that is immediately perceivable.

For controlling the individual components and for detecting the measured values, the blood pump 9 is connected to the central control and computing unit 5 with a control line 9', the alarm unit 19 with a control line 19', the arterial and venous cut-off units 16, 17 with control lines 16', 17', and the arterial and venous pressure sensors 18A, 18B with control lines 18A', 18W.

The control and computing unit 15 is programmed such that during the blood treatment the arterial and venous pressures are measured continuously with the pressure sensors 18A, 18B. For monitoring the vascular access, especially the venous access, the measured pressure values are used to calculate characteristic values that are compared to prespecified limits. The control and computing unit 15 finds that there is a possible faulty vascular access when the sum of and/or difference in the arterial and venous pressure measurements are outside of prespecified limits. This method, which is described in detail in International Patent Publication No. WO 2008/006559 A1, is only an example of one monitoring method, however. Alternatively pressure signals generated by the blood pump 9 may also be evaluated. However, it is also possible to monitor the vascular access with a moisture sensor. One monitoring device with such a moisture sensor is known from International Patent Publication No. WO 2011/116943, for instance.

If the presence of a faulty vascular access is established with the method described in the foregoing, i.e., the sum of and/or difference in the arterial and venous pressure measurements are outside of the prespecified limits, the control and computing unit 15 generates a control signal for the blood pump so that the blood pump 9 is stopped. The arterial and venous tube clamps 16, 17 remain open, however. The control and computing unit 15 further generates a control signal for the alarm unit 19 so that the first signal generator 19A provides a preliminary alarm. In addition, a timing element 15A for the control and computing unit 15 is started.

The occlusion blood pump 9 thus separates the arterial branch 6 of the extracorporeal flow from the arterial vascular access. This prevents blood from the venous puncture cannula 8 from being pumped if the venous cannula should have slipped out of the venous vascular access. This fault is now verified with a second monitoring method that differs from the first method with respect to the monitoring criteria.

In the present exemplary embodiment the second monitoring method is a method for monitoring pressure pulses that are produce by the heartbeat of the patient that is attached to the arterial and venous tubes 6, 7. When the tube clamps 16, 17 are still open, these pressure pulses produced by the heart may propagate into the tubing system so that they are detected by the arterial and venous pressure sensors 18A, 18B. Since the blood pump 9 is idle, no pressure pulses are being produced by the blood pump. Therefore essentially only the pressure pulses that are produced by the heart are detected by the arterial and venous pressure sensors. These pressure pulses are at least not overlaid by pressure pulses from the blood pump 9. In the control and computing unit 15, interfering signals are removed from the pressure pulses of the heart and the latter are then evaluated in order to be able to establish using the known methods whether there is a faulty vascular access. The detection of the pressure pulses of the heart may also include a spectral analysis of the fluctuations in pressure. International Patent Publication No. WO 97/10013 describes such a monitoring method, for instance.

The evaluation of the arterial pressure pulses in the arterial branch or of the venous pressure pulses in the venous branch of the extracorporeal flow are enough in principle for establishing a faulty vascular access. The venous pressure pulses are preferably monitored in order to be able to establish a faulty venous access on the venous side. One exemplary embodiment provides the evaluation of both the arterial pressure pulses of the heart and the venous pressure pulses of the heart.

In one exemplary embodiment, the control and computing unit 15 is embodied such that the amplitude of the pressure pulses measured in the arterial branch are compared to a first limit and the amplitude of the pressure pulses measured in the venous branch are compared to a second limit, the blood pump being restarted if the amplitude of the pressure pulses measured in the arterial branch are greater than the first limit and the amplitude of the pressure pulses measured in the venous branch are greater than the second limit. One alternative criterion for starting the blood pump may also be the measurement of only venous pressure pulses, however.

One particularly preferred embodiment provides monitoring of the frequency of both the arterial and venous pressure pulses. In this embodiment, the control and computing unit 15 is embodied such that the frequency of the arterial pressure pulses is compared to the frequency of the venous pressure pulses. If the difference in the frequencies is greater than a prespecified limit, a condition of not in proper order is found, even though both arterial and venous pressure signals are being detected.

If pressure pulses of the heart are detected in the arterial and venous branches of the extracorporeal blood flow, the control and computing unit 15 finds that there is no fault. In this case, the control and computing unit 15 generates a control signal so that the blood pump 9 is restarted to continue the blood treatment. Consequently the blood treatment has been interrupted only for a brief period, and the blood treatment continues automatically without intervention from the medical staff.

If pressure pulses from the heart are detected in the venous branch of the extracorporeal blood flow and pressure pulses are not detected in the arterial branch of the extracorporeal flow, the control and computing unit 15 also finds that there is not necessarily a fault. In this case the control and computing unit 15 generates a control signal so that the blood pump 9 is restarted to continue the blood treatment. Consequently the blood treatment has been interrupted only for a brief period, and the blood treatment continues automatically without intervention from the medical staff. In this case it is possible for there to be a preliminary alarm.

In contrast, if the pressure pulses from the heart are not detected in the venous line 7, it is found that there actually is a vascular access that is not in proper order and the blood treatment is interrupted.

A fault is also found when no pressure pulses from the heart are detected in the arterial and venous lines 16, 17. This situation will probably occur only rarely in practice, because for it to come about both cannulas would have to be disconnected at the same time.

If such a fault is suggested, the control and computing unit 15 generates a control signal for the arterial and venous cut-off units 16, 17 so that the cut-off units can be closed. Thus the arterial and venous lines 6, 7 are completely closed off from the patient. The control and computing unit 15 further generates a control signal for the alarm unit 19 so that the second signal generator 19B provides a preferably acoustic alarm. After the acoustic alarm, medical staff can take the required measures.

During verification of the previously detected fault, the control and computing unit 15 continuously monitors whether a certain time interval that is prespecified by the timing unit element has elapsed. Once the time interval has elapsed, the arterial and venous tube clamps 16, 17 are automatically closed for safety reasons. This ensures that it is only possible to verify the fault and continue the blood treatment within narrow temporal limits.

The invention claimed is:

1. A method for monitoring an extracorporeal blood circuit during an extracorporeal blood treatment using an extracorporeal blood treatment device in which blood from a patient is conveyed with a blood pump from an arterial patient connection via an arterial branch of the extracorporeal blood circuit into a blood treatment unit and out of the blood treatment unit via a venous branch of the extracorporeal blood circuit to a venous patient connection, a venous cut-off unit provided in the venous branch upstream of the venous patient connection, the method comprising:
    monitoring at least one of an arterial access or a venous access with a first method and a second method, wherein the first method and the second method check for a presence of at least one criterion that is characteristic of a faulty vascular access, wherein the at least one criterion checked by the first method and the at least one criterion checked by the second method are different;
    establishing, based on the least one criterion checked by the first method, that the vascular access is faulty;
    stopping the blood pump and keeping the venous cut-off unit open;
    checking, while the blood pump is stopped, for the presence of the least one criterion checked by the second method; and
    one of:
        closing the venous cut-off unit if the at least one criterion checked by the second method is present; and
        restarting the blood pump if the at least one criterion checked by the second method is not present.

2. The method according to claim 1, further comprising:
    providing an arterial cut-off unit in the arterial branch downstream of the arterial patient connection;
    keeping the arterial and venous cut-off units open if the presence of the at least one criterion checked by the first method has been established;
    checking, while the blood pump has been stopped, for the presence of the at least one criterion checked by the second method; and
    one of:
        closing the arterial and venous cut-off units if the at least one criterion checked by the second method is present; and
        restarting the blood pump if the at least one criterion checked by the second method is not present.

3. The method according to claim 1, further comprising:
    generating an alarm if the presence of the at least one criterion checked by the second method has been established.

4. The method according to claim 1, further comprising:
    generating a first alarm if the presence of the at least one criterion checked by the first method has been established; and generating a second alarm signal if the presence of the at least one criterion checked by the second method has been established.

5. The method according to claim 1, wherein the at least one criterion checked by at least one of the first or second method is a change in a characteristic variable that is measured in at least one of the arterial or venous branch of the extracorporeal blood circuit or is a change in a characteristic variable that is measured at, at least one of a venous or arterial puncture site.

6. The method according to claim 5, wherein the characteristic variable is a change in the pressure or a change in pressure pulses in at least one of the arterial or venous branch of the extracorporeal blood circuit and based on a condition of at least one of the arterial or venous access.

7. The method according to claim 1, wherein the at least one criterion checked by the second method is a change in pressure pulses measured in at least one of the arterial or venous branch of the extracorporeal blood circuit, which pressure pulses derive from a physiological event in the patient connected to the extracorporeal blood circuit.

8. The method according to claim 7, wherein the physiological event is a heartbeat of the patient.

9. The method according to claim 8, wherein:
pressure pulses produced by the heartbeat of the patient are measured in the arterial and venous branches of the extracorporeal blood circuit;
at least one of the amplitude of the pressure pulses measured in the arterial branch are compared to at least one of a first limit or the amplitude of the pressure pulses measured in the venous branch are compared to a second limit; and
the blood pump is restarted if both the amplitude of the pressure pulses measured in the arterial branch are greater than the first limit and the amplitude of the pressure pulses measured in the venous branch are greater than the second limit.

10. The method according to claim 1, further comprising:
checking, when the blood pump is stopped, if a predetermined time interval that begins when the blood pump is stopped has elapsed; and
closing the venous cut-off unit after the time interval has elapsed.

11. A device for monitoring an extracorporeal blood circuit during an extracorporeal blood treatment using an extracorporeal blood treatment device in which blood from a patient is conveyed with a blood pump from an arterial patient connection via an arterial branch of the extracorporeal blood circuit into a blood treatment unit and out of the blood treatment unit via a venous branch of the extracorporeal blood circuit to a venous patient connection, a venous cut-off unit provided in the venous branch upstream of the venous patient connection, the device for monitoring comprising:
a control and computing unit configured to implement the method of claim 1.

12. The device according to claim 11, further comprising:
an arterial cut-off unit provided in the arterial branch downstream of the arterial patient connection, wherein the control and computing unit is configured to:
keep the arterial and venous cut-off units open if the presence of the at least one criterion checked by the first method has been established;
check, while the blood pump has been stopped, for the presence of the at least one criterion checked by the second method; and
one of:
close the arterial and venous cut-off units if the at least one criterion checked by the second method is present; and
restart the blood pump if the at least one criterion checked by the second method is not present.

13. The device according to claim 11, further comprising:
an alarm unit, wherein the control and computing unit is configured to generate an alarm if the presence of the at least one criterion checked by the second method has been established.

14. The device according to claim 11, further comprising:
a first alarm unit and a second alarm unit, wherein the control and computing unit is configured to:
generate a first alarm if the presence of the at least one criterion checked by the first method has been established; and
generate a second alarm signal if the presence of the at least one criterion checked by the second method has been established.

15. The device according to claim 11, wherein the at least one criterion checked by at least one of the first or second method is a change in a characteristic variable that is measured in at least one of the arterial or venous branch of the extracorporeal blood circuit or is a change in a characteristic variable that is measured at, at least one of a venous or arterial puncture site.

16. The device according to claim 15, wherein the characteristic variable is a change in the pressure or a change in pressure pulses in at least one of the arterial or venous branch of the extracorporeal blood circuit and is based on a condition of at least one of the arterial or venous access.

17. The device according to claim 11, wherein the at least one criterion checked by the second method is a change in pressure pulses measured in at least one of the arterial or venous branch of the extracorporeal blood circuit, which pressure pulses derive from a physiological event in the patient connected to the extracorporeal blood flow.

18. The device according to claim 17, wherein the physiological event is a heartbeat of the patient.

19. The device according to claim 18, further comprising:
a pressure measuring unit, wherein the control and computing device is configured such that:
the pressure pulses produced by the heartbeat of the patient are measured in the arterial and venous branches of the extracorporeal blood circuit;
at least one of the amplitude of the pressure pulses measured in the arterial branch are compared to at least one of a first limit or the amplitude of the pressure pulses measured in the venous branch are compared to a second limit; and
the blood pump is restarted if both the amplitude of the pressure pulses measured in the arterial branch are greater than the first limit and the amplitude of the pressure pulses measured in the venous branch are greater than the second limit.

20. The device according to claim 11, further comprising:
a timing element, wherein the control and computing unit is configured such that:
when the blood pump is stopped, the timing element is started; and
a control signal for closing the venous cut-off unit is generated when the time interval has elapsed.

21. The device according to claim 11, wherein the blood pump is an occlusion pump.

* * * * *